(12) United States Patent
Frenkel et al.

(10) Patent No.: US 8,614,252 B2
(45) Date of Patent: Dec. 24, 2013

(54) CRYSTALLINE SOLID RASAGILINE BASE

(75) Inventors: Anton Frenkel, Netanya (IL); Tamas Koltai, Netanya (IL)

(73) Assignee: Teva Pharmaceutical Industries Ltd., Petach-Tikva (IL)

( * ) Notice: Subject to any disclaimer, the term of this patent is extended or adjusted under 35 U.S.C. 154(b) by 484 days.

(21) Appl. No.: 12/655,827

(22) Filed: Jan. 8, 2010

(65) Prior Publication Data

US 2010/0145101 A1 Jun. 10, 2010

Related U.S. Application Data

(62) Division of application No. 12/002,082, filed on Dec. 13, 2007, now Pat. No. 7,750,051.

(60) Provisional application No. 60/875,011, filed on Dec. 14, 2006.

(51) Int. Cl.
 - *A01N 33/02* (2006.01)
 - *A61K 31/135* (2006.01)
 - *C07C 211/00* (2006.01)

(52) U.S. Cl.
 USPC ............................ 514/647; 514/657; 564/308

(58) Field of Classification Search
 None
 See application file for complete search history.

(56) References Cited

U.S. PATENT DOCUMENTS

| | | | |
|---|---|---|---|
| 4,252,951 A * | 2/1981 | Jackson et al. ............... | 540/220 |
| 4,529,811 A | 7/1985 | Hill et al. | |
| 5,387,612 A | 2/1995 | Youdim et al. | |
| 5,453,446 A | 9/1995 | Youdim et al. | |
| 5,457,133 A | 10/1995 | Youdim et al. | |
| 5,486,541 A | 1/1996 | Sterling et al. | |
| 5,519,061 A | 5/1996 | Youdim et al. | |
| 5,532,415 A | 7/1996 | Youdim et al. | |
| 5,576,353 A | 11/1996 | Youdim et al. | |
| 5,599,991 A | 2/1997 | Youdim et al. | |
| 5,663,415 A | 9/1997 | Chopdekar et al. | |
| 5,668,181 A | 9/1997 | Youdim et al. | |
| 5,744,500 A | 4/1998 | Youdim et al. | |
| 5,786,390 A | 7/1998 | Youdim et al. | |
| 5,891,923 A | 4/1999 | Youdim et al. | |
| 6,126,968 A | 10/2000 | Peskin et al. | |
| 6,271,263 B1 | 8/2001 | Sklarz et al. | |
| 6,277,886 B1 | 8/2001 | Levy et al. | |
| 6,316,504 B1 | 11/2001 | Youdim et al. | |
| 6,462,222 B1 | 10/2002 | Chorev et al. | |
| 6,630,514 B2 | 10/2003 | Youdim et al. | |

(Continued)

FOREIGN PATENT DOCUMENTS

| EP | 1561461 | 8/2005 |
|---|---|---|
| WO | WO 95/11016 | 4/1995 |

(Continued)

OTHER PUBLICATIONS

Morissette et al. Advanced Drug Delivery Reviews 2004, 56, 275-300.*

(Continued)

*Primary Examiner* — Clinton Brooks

(74) *Attorney, Agent, or Firm* — John P. White; Gary J. Gershik; Cooper & Dunham LLP

(57) ABSTRACT

The subject invention provides crystalline R(+)-N-propargyl-1-aminoindan, pharmaceutical compositions and methods of manufacture thereof.

9 Claims, 12 Drawing Sheets

(56) References Cited

U.S. PATENT DOCUMENTS

| | | | |
|---|---|---|---|
| 6,635,667 | B2 | 10/2003 | Thomas |
| 6,956,060 | B2 | 10/2005 | Youdim et al. |
| 7,309,497 | B2 | 12/2007 | Rimpler et al. |
| 7,396,860 | B2 | 7/2008 | Blaugrund et al. |
| 7,491,847 | B2 | 2/2009 | Frenkel |
| 7,547,806 | B2 | 6/2009 | Frenkel et al. |
| 7,572,834 | B1 | 8/2009 | Sterling et al. |
| 7,598,420 | B1 | 10/2009 | Sterling et al. |
| 7,619,117 | B1 | 11/2009 | Lidor-Hadas et al. |
| 7,750,051 | B2 | 7/2010 | Frenkel et al. |
| 7,815,942 | B2 | 10/2010 | Peskin |
| 7,855,233 | B2 | 12/2010 | Frenkel et al. |
| 7,968,749 | B2 | 6/2011 | Frenkel et al. |
| 8,080,584 | B2 | 12/2011 | Safadi et al. |
| 8,334,409 | B2 | 12/2012 | Frenkel |
| 2003/0014879 | A1 | 1/2003 | Horigane et al. |
| 2003/0087814 | A1 | 5/2003 | Lederman |
| 2003/0180332 | A1 | 9/2003 | Rimpler et al. |
| 2004/0127577 | A1 | 7/2004 | Blaugrund et al. |
| 2004/0157784 | A1 | 8/2004 | Chopdekar et al. |
| 2005/0239054 | A1 | 10/2005 | Arimilli et al. |
| 2006/0018957 | A1 | 1/2006 | Lerner et al. |
| 2006/0094783 | A1 | 5/2006 | Youdim et al. |
| 2006/0142374 | A1 | 6/2006 | Tsuru et al. |
| 2006/0188581 | A1 | 8/2006 | Peskin |
| 2006/0276503 | A1 | 12/2006 | Breen et al. |
| 2007/0100001 | A1 | 5/2007 | Youdim et al. |
| 2007/0112217 | A1 | 5/2007 | Frenkel et al. |
| 2007/0116729 | A1 | 5/2007 | Palepu |
| 2007/0232700 | A1 | 10/2007 | Blaugrund et al. |
| 2008/0038833 | A1 | 2/2008 | Popp |
| 2008/0161408 | A1 | 7/2008 | Frenkel et al. |
| 2009/0062400 | A1 | 3/2009 | Oron et al. |
| 2009/0076160 | A1 | 3/2009 | Lendvai et al. |
| 2009/0181086 | A1 | 7/2009 | Safadi et al. |
| 2010/0008983 | A1 | 1/2010 | Safadi et al. |
| 2010/0010095 | A1 | 1/2010 | Frenkel et al. |
| 2010/0137447 | A1 | 6/2010 | Lehmann et al. |
| 2010/0144887 | A1 | 6/2010 | Frenkel et al. |
| 2010/0168239 | A1 | 7/2010 | Poewe |
| 2010/0189788 | A1 | 7/2010 | Safadi et al. |
| 2010/0189790 | A1 | 7/2010 | Safadi et al. |
| 2010/0189791 | A1 | 7/2010 | Safadi et al. |
| 2010/0234636 | A1 | 9/2010 | Stahl |
| 2011/0130466 | A1 | 6/2011 | Lorenzl |
| 2011/0152381 | A1 | 6/2011 | Frenkel et al. |
| 2011/0313050 | A1 | 12/2011 | Rimkus et al. |
| 2012/0003310 | A1 | 1/2012 | Safadi et al. |
| 2012/0029087 | A1 | 2/2012 | Petit et al. |
| 2012/0059058 | A1 | 3/2012 | Lorimer et al. |
| 2012/0100189 | A1 | 4/2012 | Safadi et al. |
| 2012/0101168 | A1 | 4/2012 | Bahar et al. |
| 2012/0238636 | A1 | 9/2012 | Patashnik et al. |
| 2012/0263789 | A1 | 10/2012 | Safadi et al. |

FOREIGN PATENT DOCUMENTS

| | | |
|---|---|---|
| WO | WO 96/23760 | 8/1996 |
| WO | WO 02/068376 | 9/2002 |
| WO | WO 2006/057912 | 1/2006 |
| WO | WO 2006/091657 | 8/2006 |
| WO | WO 2007/098264 | 2/2007 |
| WO | WO 2007/101400 | 9/2007 |
| WO | WO 2008/019871 | 2/2008 |
| WO | WO 2008/076315 | 6/2008 |
| WO | WO 2008/076348 | 6/2008 |
| WO | WO 2008/131961 | 11/2008 |
| WO | WO 2009/122301 | 10/2009 |
| WO | WO 2011/003938 | 1/2011 |

OTHER PUBLICATIONS

Vippagunta et al. Advanced Drug Delivery Reviews 2001, 48, 3-26.*

West, Anthony R., "Solid State Chemistry and its Applications", Wiley, New York, 1988, pp. 358 & 365.*

Braga et al., "Making crystals from crystals: a green route to crystal engineering and polymorphism" ChemComm 2005, 3635-3645.*

Feb. 5, 2010 Amendment filed in response to the Nov. 2, 2009 European Search Report issued in European Patent Application No. EP 07862906.0.

Eurasian Search Report mailed Jan. 25, 2010 in connection with Eurasian Patent Application No. 200970581.

U.S. Appl. No. 11/791,684, filed May 24, 2007 (including specification and pending claim set).

U.S. Appl. No. 12/002,076, filed Dec. 13, 2007 (including specification and pending claim set).

U.S. Appl. No. 12/223,794, filed Aug. 7, 2008 (including specification and pending claim set).

U.S. Appl. No. 12/283,946, filed Sep. 16, 2008 (including specification and pending claim set).

U.S. Appl. No. 12/231,601, filed Sep. 3, 2008 (including specification and pending claim set).

U.S. Appl. No. 12/319,576, filed Jan. 9, 2009 (including specification and pending claim set).

U.S. Appl. No. 12/456,166, filed Jun. 12, 2009 (including specification and pending claim set).

U.S. Appl. No. 12/456,642, filed Jun. 19, 2009 (including specification and pending claim set).

U.S. Appl. No. 12/456,643, filed Jun. 19, 2009 (including specification and pending claim set).

U.S. Appl. No. 12/455,969, filed Jun. 10, 2009 (including specification and pending claim set).

U.S. Appl. No. 12/456,029, filed Jun. 9, 2009 (including specification and pending claim set).

U.S. Appl. No. 12/456,031, filed Jun. 9, 2009 (including specification and pending claim set).

U.S. Appl. No. 12/455,976, filed Jun. 9, 2009 (including specification and pending claim set).

U.S. Appl. No. 12/456,001, filed Jun. 9, 2009 (including specification and pending claim set).

U.S. Appl. No. 12/283,022, filed Sep. 8, 2008 (including specification and pending claim set).

U.S. Appl. No. 12/283,107, filed Sep. 8, 2008 (including specification and pending claim set).

U.S. Appl. No. 12/283,105, filed Sep. 8, 2008 (including specification and pending claim set).

Office Action issued Jul. 11, 2008 in the U.S. Appl. No. 12/002,076.

Office Action issued Jul. 11, 2008 in connection with U.S. Patent No. 7,547,806.

Apr. 28, 2008 International Search Report in connection with the related PCT International Application No. PCT/US2007/025516.

International Search Report of PCT International Application No. PCT/US2007/25583, file Dec. 13, 2007.

Jun. 16, 2009 International Preliminary Report on Patentability and the Written Opinion of the Intl. Searching Authority for Intl. Application No. PCT/US07/025583.

Aug. 18, 2009 International Search Report and Written Opinion of the International Searching Authority for International Application No. PCT/US2009/03677.

Oct. 5, 2009 International Search Report and Written Opinion of the International Searching Authority for International Application No. PCT/US2009/03670.

Extended European Search Report for European Patent Application No. 07862906.0, issued Nov. 2, 2009.

Azilect®, Physician's Desk Reference (2006), 60th Edition, Thomson Healthcare.

Morissette et al. (2004) "High-throughput crystallization: polymorphs, salts, co-crystals and solvates of pharmaceutical solids", Advanced Drug Delivery Reviews, 56, 275-300.

Vippagunta et al. (2001) "Crystalline solids", Advanced Drug Discovery Review, 48, 3-26, abstract.

Office Action issued May 8, 2009 in connection with U.S. Appl. No. 12/002,082.

Office Action issued Jul. 8, 2009 in connection with U.S. Appl. No. 12/002,082.

Office Action issued Jan. 17, 2012 in U.S. Appl. No. 12/655,828.

Republic of South Africa Patent No. 2009/03903, issued Aug. 25, 2010.

(56) References Cited

OTHER PUBLICATIONS

May 17, 2011 Office Action issued in connection with Eurasian Patent Application No. 200970581.
Jan. 24, 2011 Office Action issued connection with European Patent Application No. 07 862 906.
Sep. 6, 2010 Office Action issued in connection with New Zealand Patent Application No. 577460.
Aug. 5, 2011 Office Action issued in connection with New Zealand Patent Application No. 577460.
Oct. 11, 2011 Response to May 17, 2011 Office Action issued in connection with Eurasian Patent Application No. 200970581.
Mar. 9, 2011 Response to Jan. 24, 2011 Office Action issued connection with European Patent Application No. 07 862 906.0.
Aug. 3, 2011 Response to Sep. 6, 2010 Office Action issued in connection with New Zealand Patent Application No. 577460.
Dec. 2, 2011 Response to Aug. 5, 2011 Office Action issued in connection with New Zealand Patent Application No. 577460.
U.S. Appl. No. 13/651,307, filed Oct. 12, 2012, Levy et al.
U.S. Appl. No. 13/647,658, filed Oct. 9, 2012, Ulanenko et al.
U.S. Appl. No. 13/647,685, filed Oct. 9, 2012, Safadi et al.
U.S. Appl. No. 13/647,622, filed Oct. 9, 2012, Safadi et al.
Caira, "Crystalline Polymorphism of Organic Compounds", in Topics in Current Chemistry vol. 196, 1998, pp. 163-208.
Apr. 15, 2012 Response to Office Action issued Jan. 17, 2012 in U.S. Appl. No. 12/655,828.
Jun. 29, 2012 Office Action in U.S. Appl. No. 12/655,828.
Dec. 19, 2012 Response to Jun. 29, 2012 Office Action in U.S. Appl. No. 12/655,828.
Mar. 19, 2012 First Official Action issued in connection with Chinese Patent Application No. 200780045866.2, filed Jun. 8, 2009 (w/English translation).
Response to Mar. 19, 2012 First Official Action issued in connection with Chinese Patent Application No. 200780045866.2, filed Jun. 8, 2009.
Aug. 31, 2012 Second Official Action issued in connection with Chinese Patent Application No. 200780045866.2, filed Jun. 8, 2009 (w/English translation).
Response to Aug. 31, 2012 Second Official Action issued in connection with Chinese Patent Applicatin No. 200780045866.2, filed Jun. 8, 2009.
Jan. 11, 2013 Third Official Action issued in connection with Chinese Patent Applicatin No. 200780045866.2, filed Jun. 8, 2009 (w/English translation).
Aug. 28, 2012 First Office Action issued in connection with Australian Patent Application No. 2007334428, filed Jun. 2, 2009.
Oct. 24, 2011 Official Action issued in connection with Mexican Patent Application No. MX/a/2009/006251, filed Jun. 12, 2009.
Jan. 2, 2012 Response to Oct. 24, 2012 Official Action issued in connection with Mexican Patent Application No. MX/a/2009/006251, filed Jun. 12, 2009.
Nov. 24, 2012 First Official Action issued by Indian Patent Office in connection with Indian Patent Application No. 1170/MUMNP/2009, filed Jun. 19, 2009.
Apr. 2, 2013 Office Action issued in connection with Japanese Patent Application No. 2009-541390, filed Jun. 12, 2009 pp. 1-9.
Reddy et al. "Dirhodium Tetracarboxylates Derived from Adamantylglycine as Chiral Catalysts for Enantioselective C-H Aminations," Supporting Information, Organic Letters, 2006 8(22):5013-5016 S2-S25.
"Dispensing Pharmacy—Basics and Applications" Nanzando Co., LTd., Sep. 20, 1977, pp. 142-145.
"New Galencial Pharmacy," Nanzando Co., Ltd., Apr. 25, 1984, 102-103 and 232-233.
"New Pharmaceutics Introduction (Third Revised Edition)" Apr. 10, 1987, Nankodo Co., Ltd. p. 111.
Mar. 25, 2013 Response to Jan. 11, 2013 Third Official Action issued in connection with Chinese Patent Application No. 200780045866.2, filed Jun. 8, 2009 pp. 1-8.
Jan. 11, 2013 Third Official Action issued in connection with Chinese Patent Applicatin No. 200780045866.2, filed Jun. 8, 2009 (with English translation of full Official Action) pp. 1-16.

\* cited by examiner

CRYSTALLINE SOLID RASAGILINE BASE

This application is a divisional of U.S. Ser. No. 12/002,082, filed Dec. 13, 2007 now U.S. Pat. No. 7,750,051, which claims benefit of U.S. Provisional Application No. 60/875,011, filed Dec. 14, 2006, the contents of all of which are hereby incorporated by reference.

Throughout this application various publications, published patent applications and published patents are referenced. The disclosures of these publications in their entireties are hereby incorporated by reference into this application in order to more fully describe the state of the art to which this invention pertains.

BACKGROUND OF THE INVENTION

U.S. Pat. Nos. 5,532,415, 5,387,612, 5,453,446, 5,457,133, 5,599,991, 5,744,500, 5,891,923, 5,668,181, 5,576,353, 5,519,061, 5,786,390, 6,316,504, 6,630,514 disclose R(+)-N-propargyl-1-aminoindan ("R-PAI"), also known as rasagiline. Rasagiline has been reported to be a selective inhibitor of the B-form of the enzyme monoamine oxidase ("MAO-B") and is useful in treating Parkinson's disease and various other conditions by inhibition of MAO-B in the brain. U.S. Pat. No. 6,126,968 and PCT publication WO 95/11016 disclose pharmaceutical compositions comprising rasagiline salts.

Rasagiline mesylate is approved for treating Parkinson's disease either as monotherapy or as an adjunct with other treatments. See, e.g. AGILECT®, Physician's Desk Reference (2006), 60$^{th}$ Edition, Thomson Healthcare.

A synthesis of rasagiline is disclosed in U.S. Pat. No. 5,532,415 in which example 3 describes recovery of rasagiline base as an oil after chromatographic separation. The other synthetic examples in U.S. Pat. No. 5,532,415 show rasagiline salt preparation from its crude form or its racemic form which is further reacted with appropriate acids to form pharmaceutically acceptable salts.

However, the existence or preparation of a crystalline form of rasagiline free base is not disclosed in the art.

SUMMARY OF THE INVENTION

The subject invention provides crystalline R(+)-N-propargyl-1-aminoindan.

The subject invention also provides a process for manufacture of crystalline R(+)-N-propargyl-1-aminoindan which comprises: a) dissolving a salt of R(+)-N-propargyl-1-aminoindan in water to form a solution; b) cooling said solution to a temperature of about 0-15° C.; c) basifying said solution to a pH of about 11 to form a suspension; and d) obtaining said crystalline rasagiline R(+)-N-propargyl-1-aminoindan from the suspension.

The subject invention also provides a process for manufacture of crystalline R(+)-N-propargyl-1-aminoindan which comprises: a) obtaining a first organic solution of liquid R(+)-N-propargyl-1-aminoindan; b) completely evaporating the solvent from the first organic solution under vacuum to form a residue; c) dissolving the residue in a second organic solvent to form a second organic solution; d) completely evaporating the second organic solvent from the second organic solution under vacuum to form a residue; and e) maintaining the second residue at a temperature between 0 and 25° C. to form crystalline R(+)-N-propargyl-1-aminoindan.

The subject invention also provides a process for manufacture of crystalline R(+)-N-propargyl-1-aminoindan which comprises: a) obtaining a solution of crystalline R(+)-N-propargyl-1-aminoindan in a water-soluble organic solvent; b) combining the solution with water; c) cooling said solution to between 0 and 20° C. to form crystalline R(+)-N-propargyl-1-aminoindan; and d) isolating the crystalline R(+)-N-propargyl-1-aminoindan.

BRIEF DESCRIPTION OF THE FIGURES

FIG. 6: Micrograph of rasagiline base prepared according to Example 8a.

DETAILED DESCRIPTION OF THE INVENTION

Figure 1:
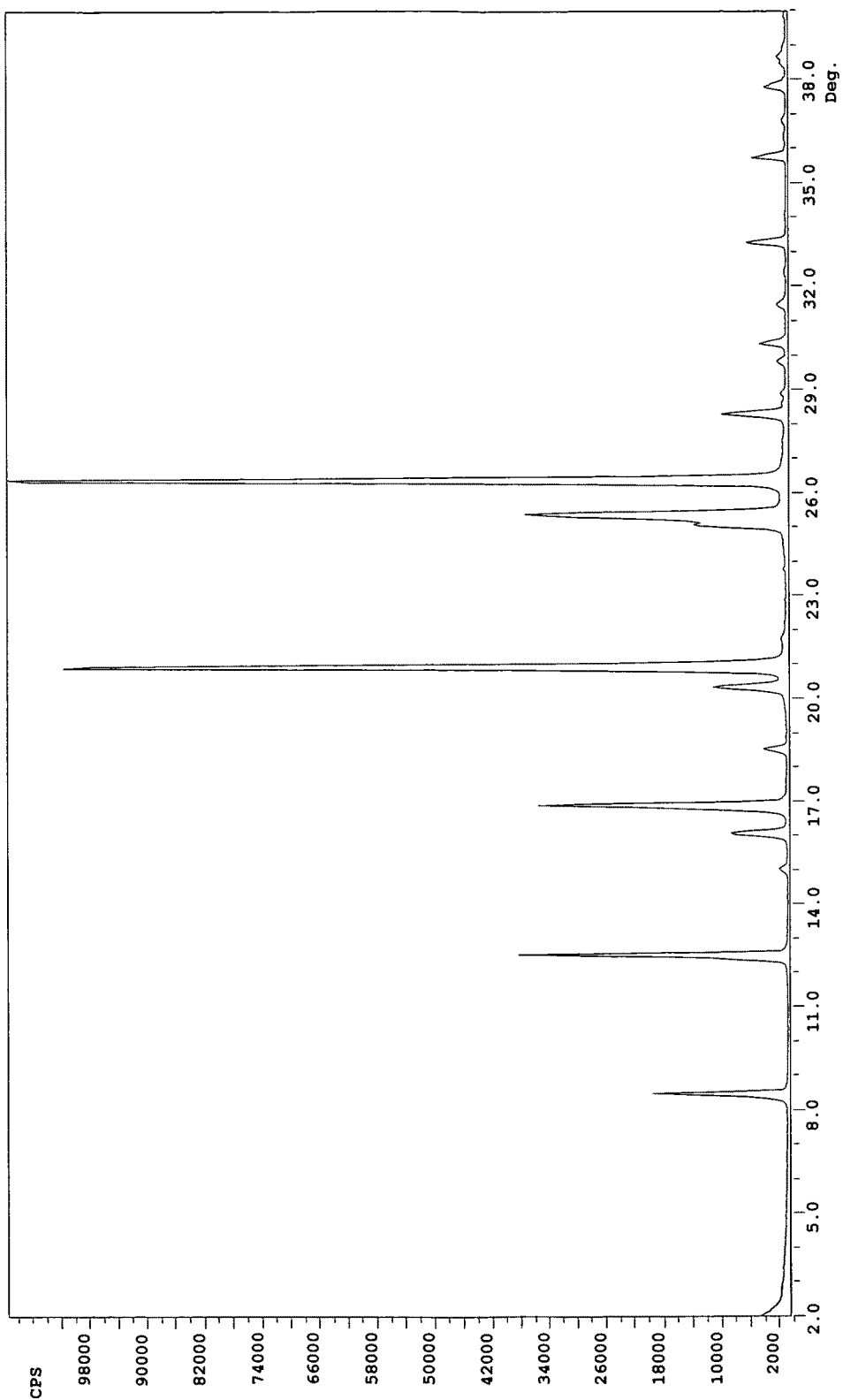
FIG. 1: X-Ray Diffraction diffractogram of rasagiline base prepared according to Example 4.
Figure 2:
FIG. 2: Micrograph of rasagiline base prepared according to Example 4.
Figure 3:
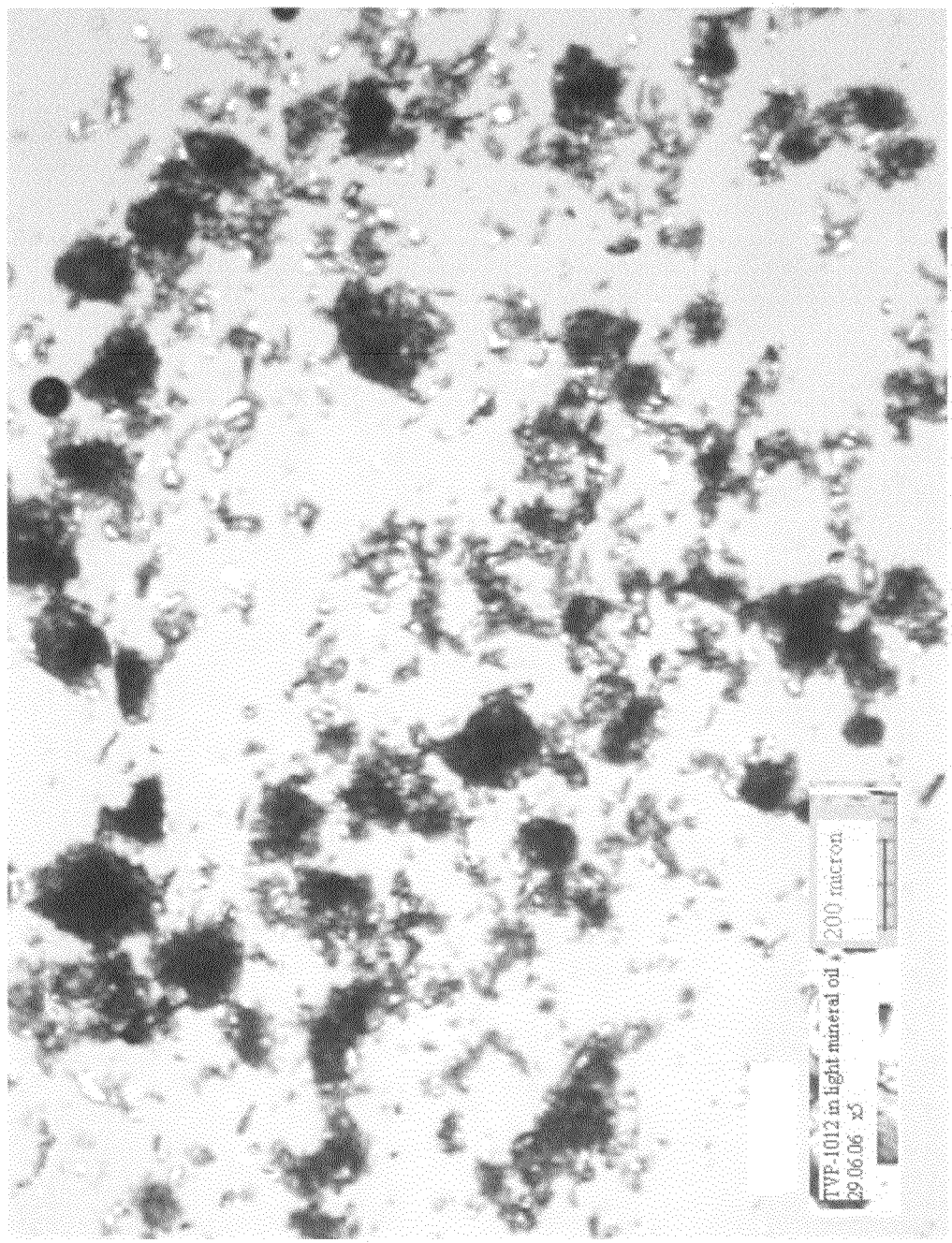
FIG. 3: Micrograph of rasagiline base prepared according to Example 5.
Figure 4:
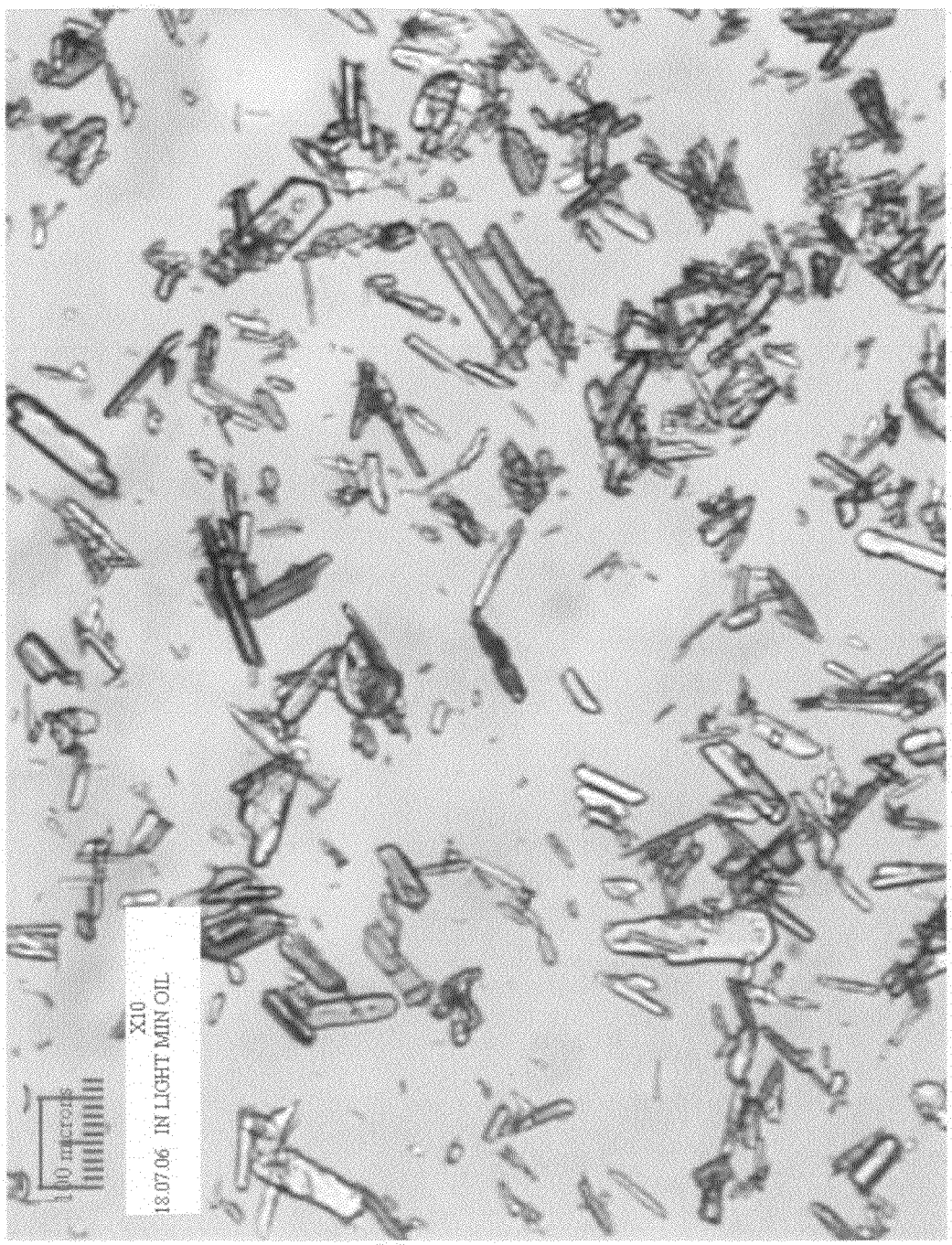
FIG. 4: Micrograph of rasagiline base prepared according to Example 6.
Figure 5:
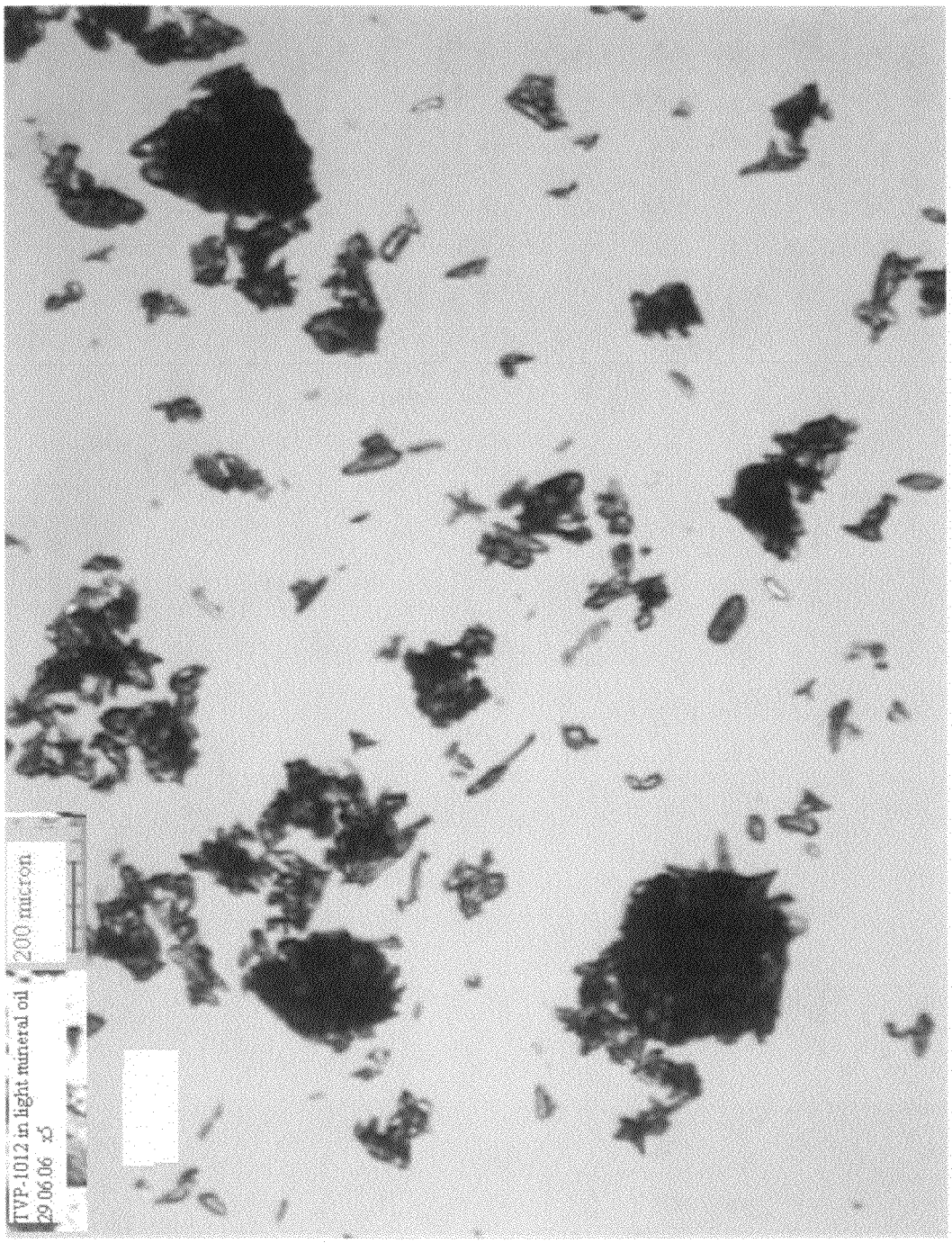
FIG. 5: Micrograph of rasagiline base prepared according to Example 7.
Figure 6:
Figure 7:
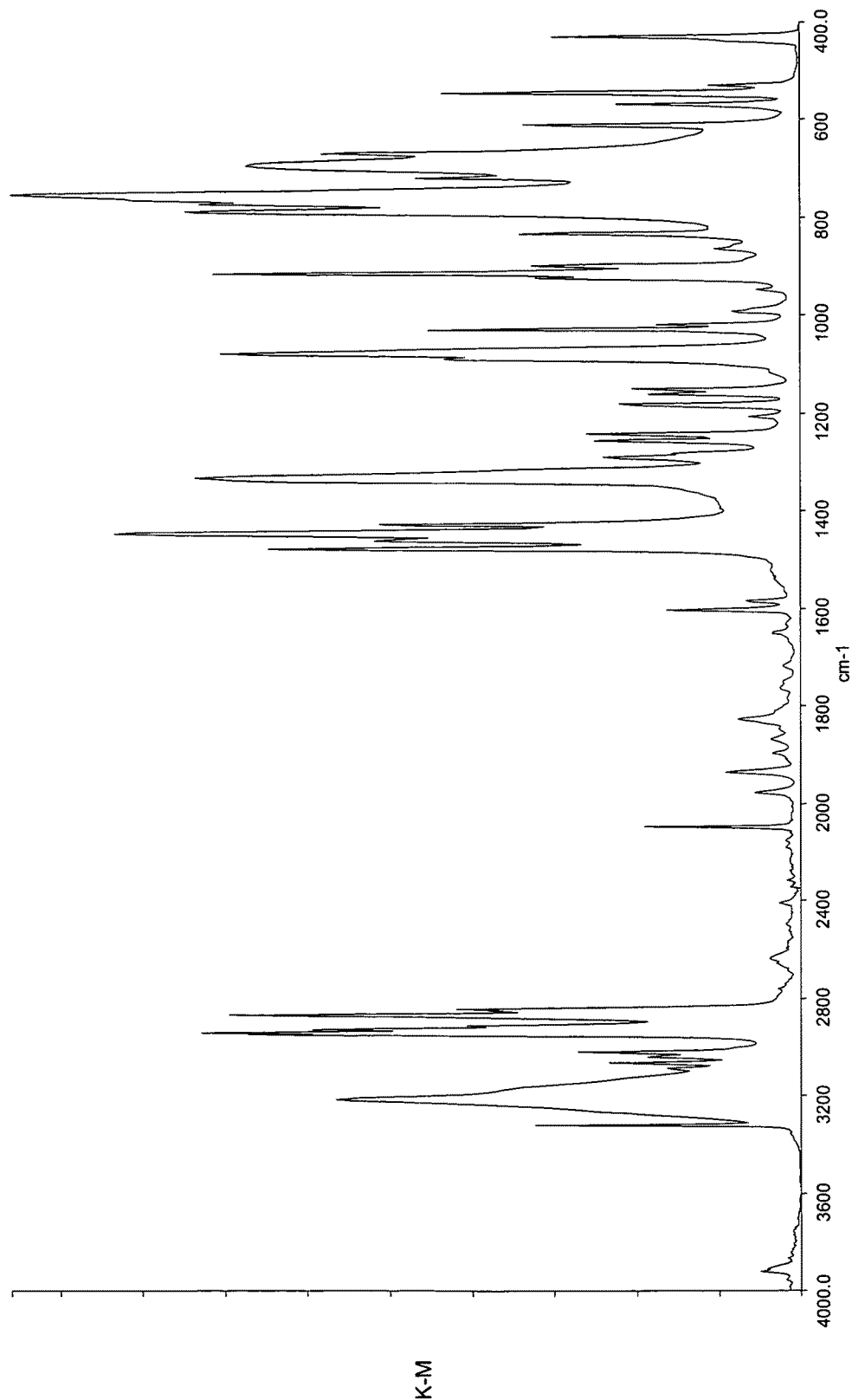
FIGS. 7-10: FTIR spectra of rasagiline base prepared according to example 5.
Figure 8:
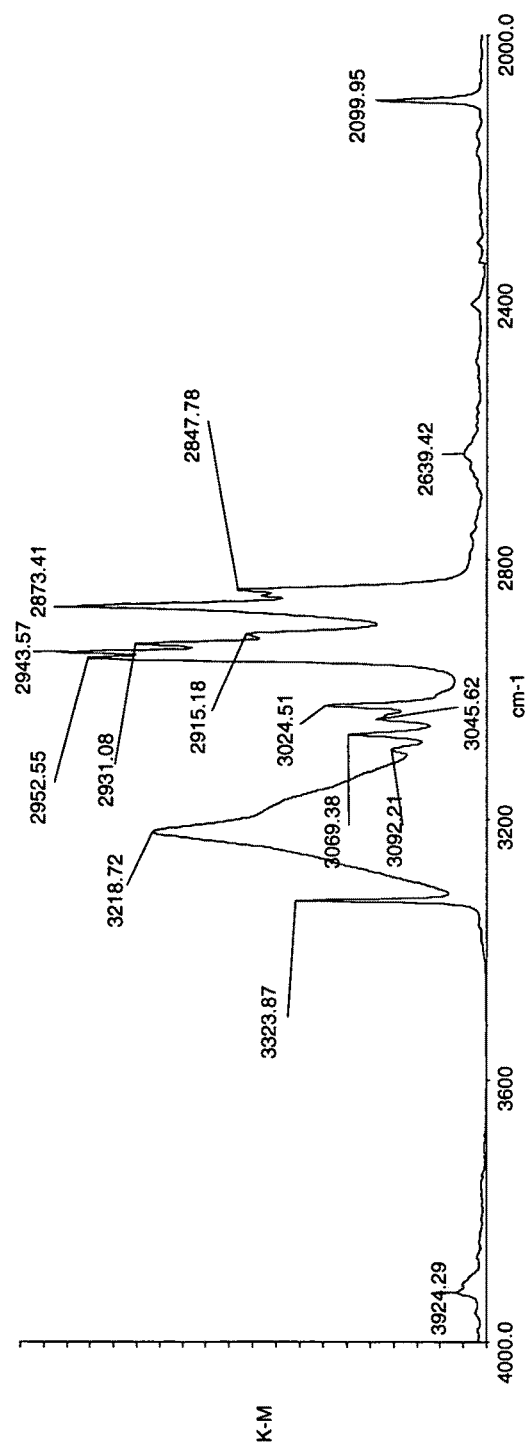
Figure 9:
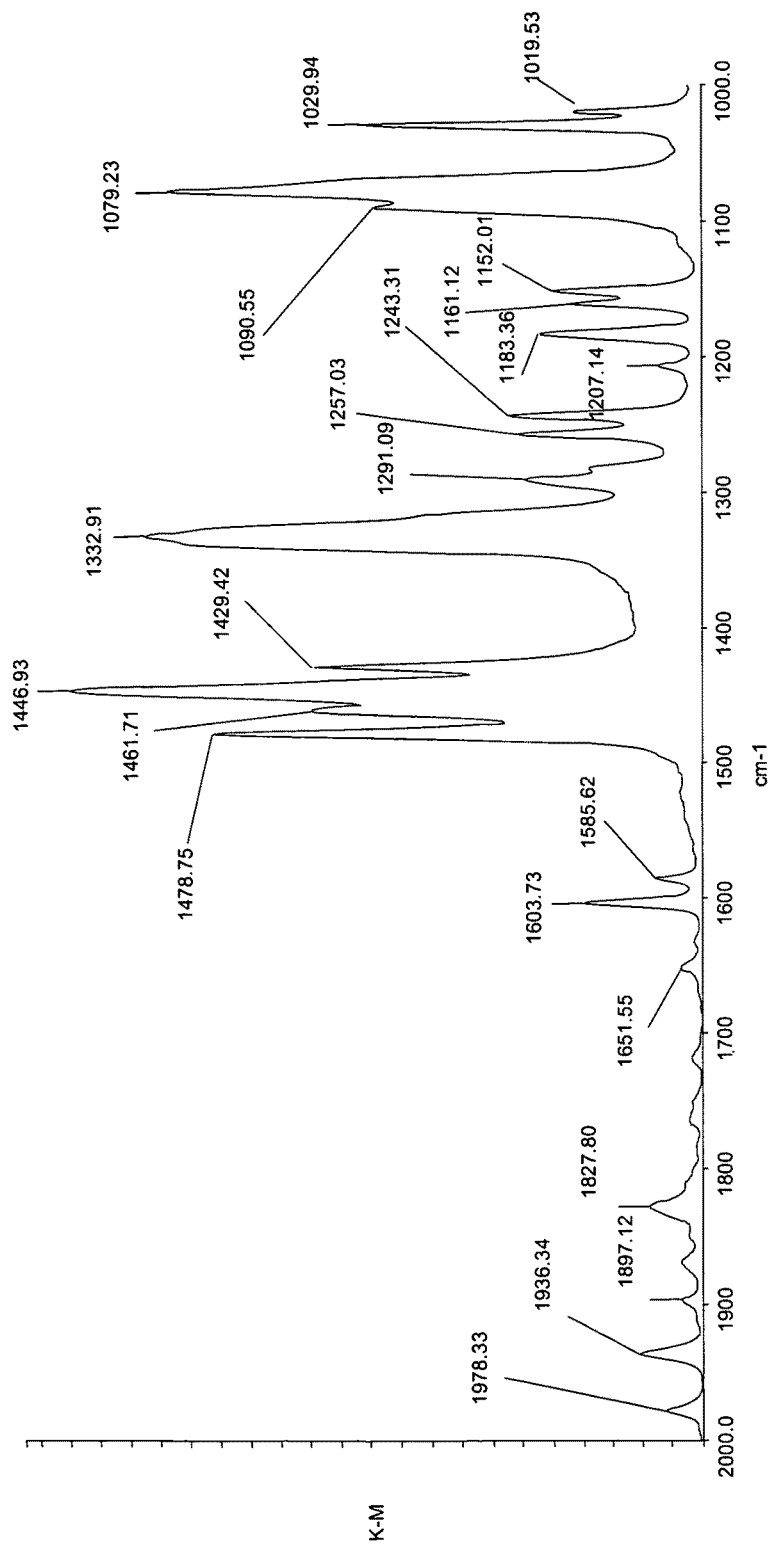
Figure 10:
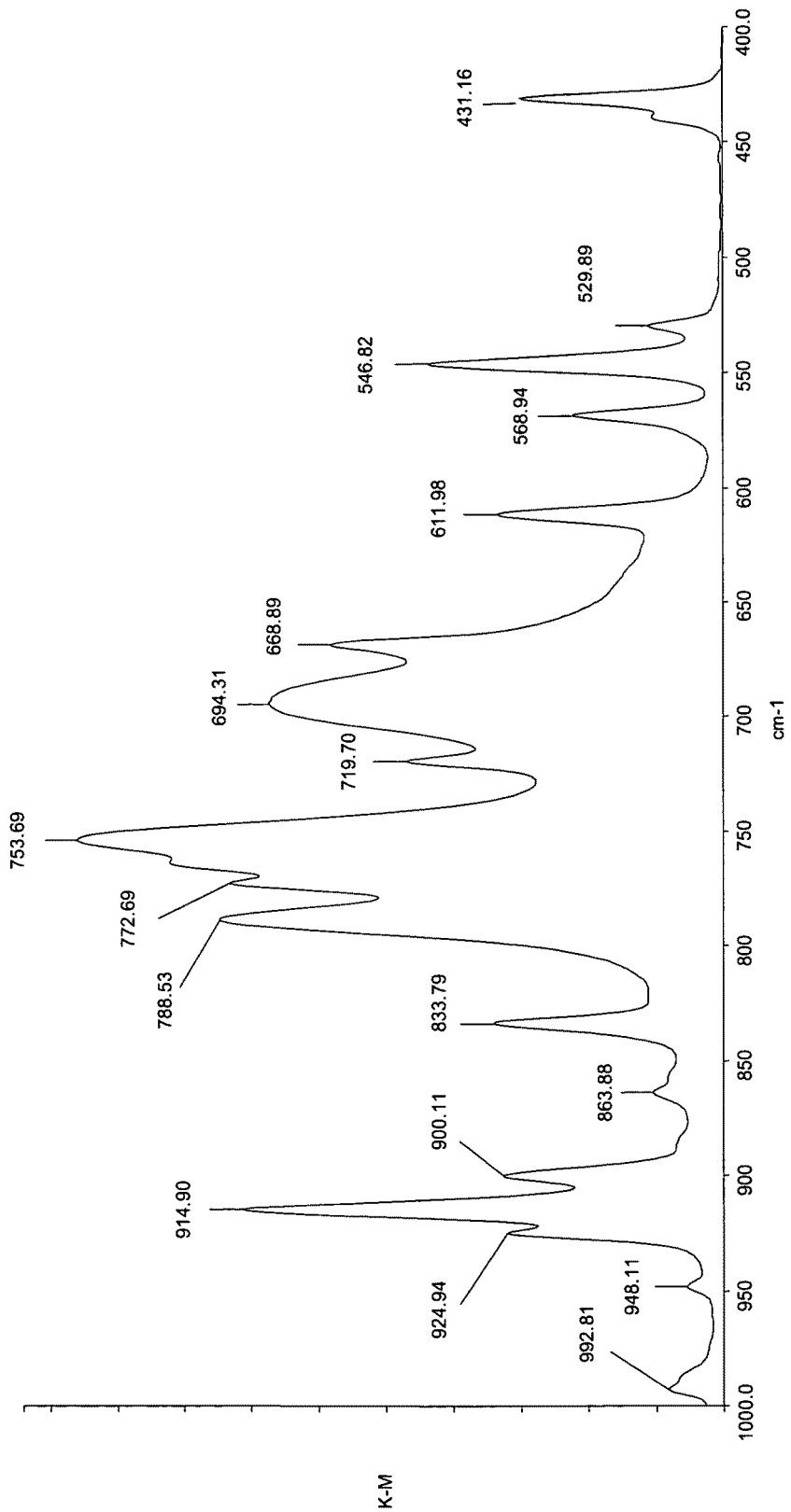

The subject invention provides crystalline R(+)-N-propargyl-1-aminoindan.

The subject invention also provides R(+)-N-propargyl-1-aminoindan characterized by a powder X-ray diffraction pattern having peaks at 8.5, 12.6, 16.1, and 16.9 in degrees two theta ±0.2. It can be further characterized by an X-ray powder diffraction pattern having peaks at 20.3; 20.9, 25.4, 26.4, and 28.3 in degrees two theta±0.2; or by a melting point of 38-41° C.

The subject invention also provides a the pharmaceutical composition comprising crystalline R(+)-N-propargyl-1-aminoindan and a pharmaceutically acceptable carrier.

The pharmaceutical composition may be formulated for transdermal application. The pharmaceutical composition may be in the form of a transdermal patch.

The subject invention also provides a process for the manufacture of crystalline R(+)-N-propargyl-1-aminoindan which comprises: a) dissolving a salt of R(+)-N-propargyl-1-aminoindan in water to form a solution; b) cooling said solution to a temperature of about 0-15° C.; c) basifying said solution to a pH of about 11 to form a suspension; and d) obtaining said crystalline rasagiline R(+)-N-propargyl-1-aminoindan from the suspension.

In an embodiment of the process, wherein the crystalline R(+)-N-propargyl-1-aminoindan is of enhanced optical purity reoative to the R(+)-N-propargyl-1-aminoindan prior to crystallization.

The subject invention also provides a process for the manufacture of crystalline R(+)-N-propargyl-1-aminoindan which comprises: a) obtaining a first organic solution of liquid R(+)-N-propargyl-1-aminoindan; b) completely evaporating the solvent from the first organic solution under vacuum to form a residue; c) dissolving the residue in a second organic solvent to form a second organic solution; d) completely evaporating the second organic solvent from the second organic solution under vacuum to form a second residue; and e) maintaining the second residue at a temperature between 0 and 25° C. to form crystalline R(+)-N-propargyl-1-aminoindan.

In an embodiment of the process, the organic solvent and the second organic solvent are the same.

In another embodiment, the organic solvent and the second organic solvent are alcohols.

In yet another embodiment, the organic solvent and the second organic solvent are isopropanol.

In yet another embodiment of the process, wherein the crystalline R(+)-N-propargyl-1-aminoindan is of enhanced optical purity reoative to the R(+)-N-propargyl-1-aminoindan prior to crystallization.

The subject invention also provides a process for manufacture of crystalline R(+)-N-propargyl-1-aminoindan which comprises: a) obtaining a solution of R(+)-N-propargyl-1-aminoindan in a water-soluble organic solvent; b) combining the solution with water; c) cooling said solution to between 0 and 20° C. to form crystalline R(+)-N-propargyl-1-aminoindan; and d) isolating the crystalline R(+)-N-propargyl-1-aminoindan.

In an embodiment of the process, the water-soluble organic solvent is an alcohol.

In another embodiment, the alcohol is either ethanol or isopropanol or a mixture of ethanol and isopropanol.

In yet another embodiment of the process, wherein the crystalline R(+)-N-propargyl-1-aminoindan is of enhanced optical purity reoative to the R(+)-N-propargyl-1-aminoindan prior to crystallization.

In development of pharmaceutical compositions, crystallinity is a desirable property in an active pharmaceutical ingredient. Crystal substances allow for ease in processing and formulating into most types of pharmaceutical dosage forms.

Previously, rasagiline base has been isolated as an oil and not as a crystalline solid. Without being bound by theory, it is possible that rasagiline has been previously isolated as an oil due to presence of residual solvents, such as toluene or isopropanol. The inventors have surprisingly found that rasagiline base may be isolated in a non-hygroscopic form that remains crystalline at room temperature.

Crystalline rasagiline base has lower water solubility than many rasagiline salts, especially the mesylate salt, which is water soluble. The solubility of rasagiline mesylate in water is 92 mg/ml at a pH of 6.7 and 570 mg/ml at a pH of 3.3, both measured at 25° C. At the same temperature, the solubility of rasagiline base in water is 5.5 mg/ml at a pH of 11.

Crystalline rasagiline base may be used as a synthetic intermediate to be used to attain a rasagiline salt, such as rasagiline mesylate or rasagiline tartrate. The crystalline rasagiline base may be dissolved in a solvent and reacted with an acid to form a pharmaceutically acceptable acid addition salt. The crystallization of rasagiline base could provide additional purification of the acid addition salt. Water solubility is often an important characteristic of an active pharmaceutical ingredient, especially when formulating oral compositions. Sometimes, lipophilicity of an active pharmaceutical ingredient is desired when formulating other pharmaceutical compositions. Crystalline rasagiline base may be useful for formulating pharmaceutical compositions wherein low solubility in water is desired. For example, compositions for transdermal administrations can be formulated from lipophilic compounds. Examples of such transdermal compositions include ointments, creams and patches.

Transdermal Formulations and Transdermal Patches

Transdermal patches are medicated adhesive patches placed on the skin to deliver a time-released dose of medication through the skin and into the bloodstream. A wide variety of pharmaceuticals can be delivered through transdermal patches, such as nicotine for smoking cessation, scopolamine for motion sickness, estrogen for menopause and prevention of osteoporosis, nitroglycerin for angina, lidocaine for pain relief from shingles. Some pharmaceuticals must be combined with other substances, such as alcohol, to increase their ability to penetrate the skin. Molecules of insulin, and many other pharmaceuticals; however, are too large to pass through the skin. Transdermal patches have several important components, including a liner to protect the patch during storage, the drug, adhesive, a membrane (to control release of the drug from the reservoir), and a backing to protect the patch from the outer environment. The two most common types of transdermal patches are matrix and reservoir types. ("Transdermal Patches", Wikipedia, Nov. 15, 2007, Wikipedia Foundation, Inc., Dec. 13, 2007 <http://en.wikipedia.org/wiki/Transdermal_patch>; and Remington, The Science and Practice of Pharmacy, 20$^{th}$ Edition, 2000)

In reservoir type patches, a drug is combined with a non-volatile, inert liquid, such as mineral oil, whereas drug in matrix type patches a drug is dispersed in a lipophilic or hydrophilic polymer matrix such as acrylic or vinylic polymers. Adhesive polymers, such as polyisobutylene, are used to hold the patch in place on the skin. (Stanley Scheindlin, (2004) "Transdermal Drug Delivery: PAST, PRESENT, FUTURE," Molecular Interventions, 4:308-312)

The major limitation to transdermal drug-delivery is the intrinsic barrier property of the skin. Penetration enhancers are often added to transdermal drug formulations in order to disrupt the skin surface and cause faster drug delivery. Typical penetration enhancers include high-boiling alcohols, diols, fatty acid esters, oleic acid and glyceride-based solvents, and are commonly added at a concentration of one to 20 percent (w/w). (Melinda Hopp, "Developing Custom Adhesive Systems for Transdermal Drug Delivery Products," Drug Delivery)

Rasagiline may also be used in combination with other drugs in a transdermal patch, such as levodopa, L-carbidopa, beserazide, ladostigil, pentahydric alcohol, hexahydric alcohol, or riluzole.

EXPERIMENTAL DETAILS

Example 1

Isolation of Rasagiline Base by Splitting and Extraction

Rasagiline mesylate was prepared essentially as described in U.S. Pat. No. 5,532,415 example 6B, with the exception that the tartrate salt was split by addition of NaOH, and the rasagiline free base was isolated as an oil. The mesylate salt was then formed by addition of methanesulfonic acid.

120 g of rasagiline mesylate were dissolved in 700 ml of deionized water. 400 ml of toluene were added and the mixture was basified with 25% NaOH solution to a pH of about 14. After stirring, two phases separated. The lower water phase was extracted with 200 ml of toluene. The phases were allowed to separate and the aqueous phase was discarded.

The two toluenic extractions were combined and the solvent was distilled under vacuum. The yield of rasagiline base was 88.5 g of a yellowish oil with a melting point of below 20° C.

25.1 g of the liquid rasagiline base was sampled. The sample was mixed with ethanol and the solvent was distilled under vacuum. 22.6 g of the rasagiline base residue, in the form of a yellowish oil remained after the ethanol evaporation. The rasagiline base in oil form remained in oil form for a number of weeks, and did not crystallize spontaneously.

Example 2

Isolation of Rasagiline Base by Splitting and Extraction 155 g of rasagiline tartrate, prepared essentially as described in U.S. Pat. No. 5,532,415 example 6B, and 20 g of rasagiline mesylate, prepared as described in example 1, were dissolved in 800 ml of water. 400 ml of toluene were added to the solution and the mixture was basified with 25% NaOH solution to a pH of about 14 and heated to 45±5° C.

After stirring, two phases were separated. The lower water phase was extracted twice with 300 ml of toluene at 45±5° C. The organic phases were combined and the aqueous phase was discarded.

The combined organic phase was washed with 200 ml of deionized water. Then the solvent was distilled under vacuum and 50 ml isopropanol were added to the resulting residue. The solvent was removed by vacuum and additional 50 ml isopropanol were added and then removed by vacuum. 100 g of syrup-like liquid rasagiline base were formed.

Example 3

Splitting and Spontaneous Crystallization From Water 15 g of rasagiline mesylate were dissolved in 150 ml water while stirring. The solution was cooled to 5° C. and 25% NaOH solution was added slowly. During the addition, batch temperature was maintained between 3 and 5° C. Solid precipitation was observed after reaching a pH of 7.5. After reaching a pH of 11, the NaOH addition was stopped, the batch was stirred while cooling for one hour and filtered. The filtration proceeded quickly. The solid product was washed with water on the filter and dried under vacuum.

8.8 g of solid dried rasagiline base were attained. The yield was 91.6%. The melting point of the solid was determined to be 38.2-38.4° C.

Example 4

Melt Crystallization 6 g of rasagiline base liquid in syrup-like form, from example 1, after toluenic evaporation were dissolved in 20 ml of isopropanol. The solution was evaporated in a warm water bath using a rotating evaporator under 12 mbar vacuum until complete solvent removal. The residue was then dissolved in an additional 20 ml of isopropanol and the evaporation was repeated. The resulting residue crystallized spontaneously at room temperature after a few hours. The solid crystalline residue was determined to be rasagiline base. 5.2 g of the solid crystalline base were attained. The yield was quantitative.

Example 5

Addition of Rasagiline Ethanolic Solution to Water 2.4 g of rasagiline base from example 1 were dissolved in 2.4 g of ethanol. The solution was added dropwise to 5 ml of cold (0-5° C.) water while stirring, and a white precipitate was formed during the addition. The resulting mixture was stirred while cooling for about 30 minutes and was filtered. The filtration proceeded quickly, and the solid product was dried to constant mass under vacuum.

2.15 g of solid crystalline rasagiline were attained, with a yield of 89.6%.

Analysis: Chromatographic purity by HPLC~100%, Assay by HPLC—99.0%.

Example 6

Addition of Water to Rasagiline Ethanolic Solution 3 g of rasagiline base from example 1 were dissolved in 5 ml of ethanol. The solution was stirred at room temperature and 4.5 ml of water were added. No precipitation occurred. The resulting solution was cooled, and at 12° C. precipitation of a white material was observed. The mixture was cooled to ~0° C., stirred at this temperature for 30 min, and filtered. The filtration proceeded quickly. The solid product was washed with water on the filter and was dried under vacuum.

2.72 g of solid crystalline rasagiline were attained, with a yield of 90.0%.

Analysis: Chromatographic purity by HPLC~100%, Assay by HPLC—100.0%.

Example 7

Addition of Rasagiline Isopropanolic Solution to Water 8.2 g of rasagiline base from example 1 were dissolved in 10 ml of isopropanol and the solution was stirred at room temperature. 14 ml of water were added. No precipitation occurred. The resulting solution was cooled, and at 17° C. precipitation of white material was observed. 20 ml of deionized water were added to the mixture and the mixture was further cooled to ~0° C., stirred at this temperature for 30 min, and filtered.

The filtration proceeded quickly. The solid product was washed with water on the filter and dried under vacuum.

5.96 g of solid crystalline rasagiline were attained, with a yield of 72.7%.

Analysis: Chromatographic purity by HPLC~100%, Assay by HPLC—99.7%

Example 8

Addition of Water to Rasagiline Isopropanolic Solution

Crop A 148 g of rasagiline base (48.0 g from example 1, and 100.0 g from example 2) were dissolved in 180 ml of isopropanol. The solution was cooled to 17° C. and 252 ml of deionized water were added at this temperature. The solution was cooled to 10° C. and seeded with solid rasagiline base. Immediate crystallization was observed. 100 ml of water were then added to the mixture. The mixture was cooled to 1° C., stirred at this temperature for 30 min and filtered. The solid was washed on the filter with 200 ml of water and dried under vacuum.

138.9 g of solid, crystalline rasagiline were attained, with a yield of 93.8%. The melting point in an open capillary was determined to be 39.0-39.2° C.

Analysis: Chromatographic purity by HPLC~100%, Assay by HPLC—98.5%.

Crop B

The mother liquor and washing liquor from crop A were combined, and solid product precipitated from the mixture. Yellowish material was separated by filtration and dried under vacuum.

1.5 g of solid, crystalline rasagiline base were attained, with a yield of 1.0%.

Discussion

The solid crystalline rasagiline base which was synthesized in examples 3-8 was found to be of high purity.

The same melting point value (41° C. by differential scanning calorimetry (DSC) or 38-39° C. in an open capillary) was measured for all batches of the crystalline rasagiline base. Low levels of volatiles (water and residual solvents) were found by Karl Fischer (KF) and by thermogravimetric analysis (TGA) methods. This indicated that crystalline rasagiline base is not hygroscopic.

Crystalline rasagiline base was found freely soluble in polar and non-polar organic solvents—alcohols, acetone, ethyl acetate, toluene, diethyl ether, dioxane, hexane and n-heptane.

All batches of solid rasagiline base were found highly crystalline by powder X-ray diffraction (XRD) and DSC method. Characteristic XRD and Fourier Transfer Infrared (FTIR) patterns and reproducible narrow melting range and enthalpy show the same polymorphic composition of all experimental batches from examples 3-8. The crystal form was designated as Form I.

The X-Ray Diffraction equipment used was a Scintag X-Ray powder diffractometer model X'TRA, Cu-tube, solid state detector.

Sample holder: a round standard aluminum sample holder with round zero background quartz plate with cavity of 25 (diameter)*0.5 (dept.) mm.

Scanning parameters: Range: 2-40 degrees two-theta.

Scan mode: Continuous scan

Step size: 0.05 deg.

Rate: 5 deg./min.

The peaks of a sample prepared according to Example 4 are listed below. The most characteristic peaks are listed in bold.

| Form I |
|---|
| 8.5 |
| 12.6 |
| 16.1 |
| 16.9 |
| 20.3 |
| 20.9 |
| 25.4 |
| 26.4 |
| 28.3 |

FTIR analysis of the samples was performed as follows:
Equipment: Perkin Elmer Spectrum One FT-IR Spectrometer S/N 58001.
Parameters: The samples were studied in DRIFT mode. All the spectra were measured in 16 scans. Resolution: 4.0 cm$^{-1}$.

All samples of solid rasagiline base prepared in this study appear as white crystalline powder (with the exception of Crop B from example which was isolated as a yellowish powder.) Microscopic observation shows that the crystallization conditions strongly affect the particle size and morphology. Seeded crystallization provides large regular non-aggregated crystals while spontaneous precipitation resulted in formation of small aggregated particles. The difference in the particle morphology is not related to polymorphism.

The morphology and particle size of the crystalline rasagiline base from the examples above is shown in the table below. The morphology and particle size was determined by microscopic observation.

| Example | Morphology | Particle Size Range (μm) |
|---|---|---|
| 4 | Irregular particles | 250-1000 |
| 5 | Small rods | 5-50 |
| 6 | Rods | 30-150 |
| 7 | Small aggregated rods | 5-50 |
| 8 | Rods | 250-2000 |

Starting Materials for Examples 9, 10 and 11:
(1) Wet Rasagiline Hemi Tartrate containing ~10-15% residual solvent and 0.7% S-isomer.
(2) Racemic RAI base, oil, PAI content—94% by HPLC.

Example 9

Splitting and Precipitation from Isopropanol-Water, Seeded Emulsion Crystallization 70.0 g of Rasagiline Tartrate salt (1) suspended in 320 ml deionized water at stirring. The suspension heated to 45° C. and 31 ml of 25% NaOH solution was added with 160 ml Toluene. The mixture was stirred and the resulting emulsion was settled. Two phases were separated. The lower aqueous phase (pH=13-14) was discarded. The upper toluenic phase was washed with 100 ml deionized water at 45° C. and settled. Lower aqueous phase (pH=9-10) was discarded.

Toluenic solution was evaporated under vacuum in evaporator, after the solvent evaporation completion 50 ml isopropanol was added to the residue and evaporation was continued.

After completion of the evaporation 25 ml of isopropanol was added and distilled out under the same conditions.

The residue, oil of R-PAI base (33.9 g); was dissolved in 41 ml isopropanol.

The solution was cooled to 15° C. and 58 ml of deionized water was added by portions in 2 hr at cooling and stirring. During the addition of water oily precipitate was formed. The resulting emulsion of oil in water was stirred at 1-3° C. for one hour, no crystallization was observed.

The batch was seeded with crystalline Rasagiline base at 1-3° C. and immediate exothermic crystallization took place. 50 ml of water was added to the resulting slurry to improve stirrability and flowability. The batch was stirred for additional 30 minutes and filtered. The solid was washed with water and dried at room temperature under vacuum.

Figure 11:
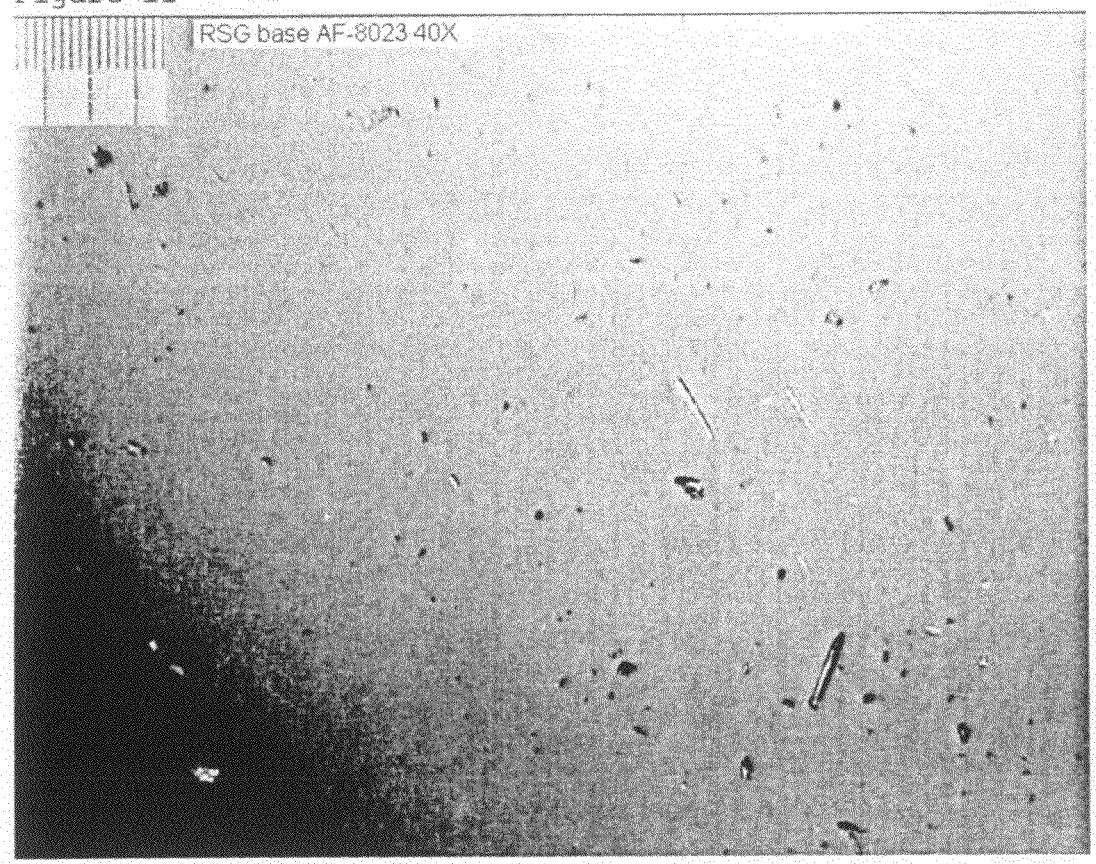
FIG. 11: Micrograph of rasagiline base prepared according to Example 9.

31.5 g of solid dry R-PAI base were attained, with a yield of 92% on oil base. FIG. 11 is a micrograph of this rasagiline base.

Analysis: Melting point (by DSC)—40.8° C., S-isomer by HPLC 0.02%, Purity by HPLC—100%, Assay by HPLC—98%.

Example 10

Splitting and Precipitation from Isopropanol-Water, Seeded Crystallization from Solution Isopropanol-Water 100.0 g of Rasagiline Tartrate (1) was suspended in 458 ml deionized water, 229 ml Toluene was added and 46 ml of 25%

NaOH solution was introduced at stirring. The mixture was heated to 45° C., stirred at 45 C for 15 minutes and settled at this temperature.

Two phases were separated. The lower aqueous phase (pH=13-14) was discarded, the upper toluenic phase was washed with 140 ml deionized water. The resulting emulsion was settled, and two phases were separated. The lower aqueous phase (pH=9-10) was discarded, the toluenic solution was evaporated under vacuum in evaporator.

After the solvent evaporation completion 60 ml isopropanol was added to the residue and evaporation was continued. After completion of the evaporation 50 ml of isopropanol was added and distilled out under the same conditions.

The residue, oil of R-PAI base (46.4 g), was dissolved in 56 ml isopropanol.

The solution was cooled to 16° C. and 147.5 ml of deionized water was added by portions in 3 hr at cooling and stirring. During the addition of water precipitation development was observed and the batch was immediately seeded with crystalline R-PAI base.

The resulting suspension was cooled to 2° C., stirred at this temperature overnight and filtered. The solid was washed with water and dried at room temperature under vacuum.

Figure 12:
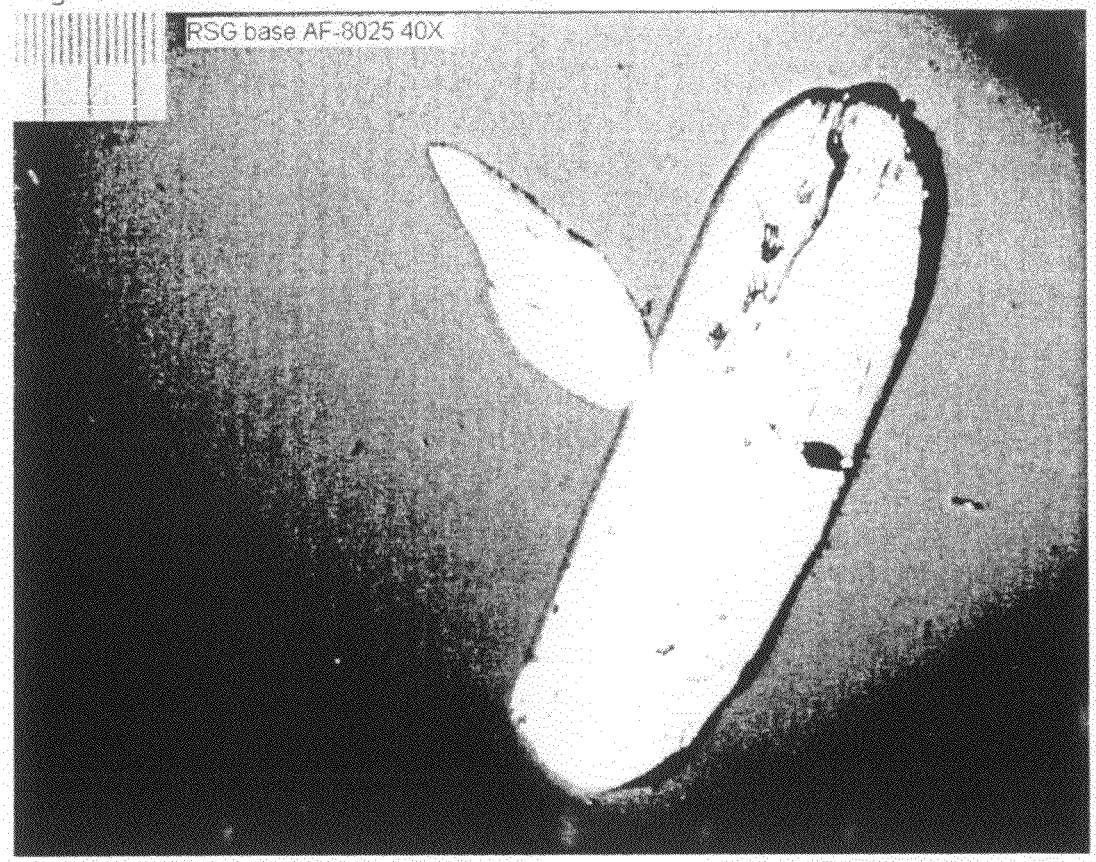
FIG. 12: Micrograph of rasagiline base prepared according to Example 10.

48.1 g of Solid dry R-PAI base were attained, with a yield of 96% on oil base. FIG. 12 is a micrograph of this rasagiline base.

Analysis: Melting point (by DSC)—41.3° C., S-isomer by HPLC 0.01%, Purity by HPLC—100%, Assay by HPLC—96%

Example 11

Racemic PAI Base Crystallization (AF-8026)
Precipitation from Isopropanol-Water 51.0 g of racemic PAI base oil (2) dissolved in 50 ml isopropanol. The solvent was distilled out of the solution under vacuum at evaporator.

The residue (49.4 g) was dissolved in 60 ml isopropanol, stirred and cooled. 156 ml of deionized water was added by portions in 3 hr at cooling and stirring. During the addition of water oily precipitate was formed. The batch was seeded with crystalline Rasagiline base, no crystallization was observed.

The resulting emulsion of oil in water was stirred at 3° C. for 1 hour, no crystallization was observed.

The batch was crystallized spontaneously during stirring overnight at 1° C. The solid was filtered, but during the filtration it began to melt. At room temperature the solid product completely liquefied on the filter in 1-2 min.

The material was sampled before the melting completion.
Analysis: S-isomer by HPLC 49.4%, Assay by HPLC—87%.
Discussion Examples 9, 10 and 11 presented above show that the ability to crystallize at room temperature is an intrinsic property of pure Rasagiline base (R-isomer). Racemic PAI base exists at room temperature only in liquid form, its melting point being between 1 and 18° C. (Example 11).

The Examples also show that crystallization of Rasagiline base contaminated with S-isomer provides significant purification of the crystallized product. Starting material containing 0.7% of S-isomer was processed into solid crystalline Rasagiline base with only 0.01-0.02% of S-isomer.

Examples 9, 10 and 11 also show the same trend in Particle Size of the crystallized product as was described in previous Examples. The slow seeded crystallization at 10-16° C. (Example 9) provides higher particle size of Rasagiline base than emulsion crystallization at 1-3° C. (Example 10).

What is claimed is:

1. A process for manufacture of crystalline R(+)-N-propargyl-1-aminoindan characterized by a powder x-ray diffraction pattern having peaks at 8.5, 12.6, 16.1, and 16.9 in degrees two theta ±0.2, comprising:
    a. obtaining a first organic solution of liquid R(+)-N-propargyl-1-aminoindan in isopropanol;
    b. completely evaporating the isopropanol from the first organic solution under vacuum to form a residue;
    c. dissolving the residue in isopropanol to form a second organic solvention;
    d. completely evaporating the isopropanol from the second organic solvention under vacuum to form a second residue; and
    e. maintaining the second residue at a temperature between 0 between and 25° C. to form crystalline R(+)-N-propargyl-1-aminoindan.

2. The process of claim 1, wherein the crystalline R(+)-N-propargyl-1-aminoindan is of enhanced optical purity relative to the R(+)-N-propargyl-1-aminoindan prior to crystallization.

3. The process of claim 1, wherein the crystalline R(+)-N-propargyl-1-aminoindan is further characterized by a melting point of 38-39° C. when determined in an open capillary or 41° C.

4. A process for manufacture of crystalline R(+)-N-propargyl-1-aminoindan characterized by a powder x-ray diffraction pattern having peaks at 8.5, 12.6, 16.1, and 16.9 in degrees two theta ±0.2, comprising:
    a. obtaining a solution of R(+)-N-propargyl-1-aminoindan in either ethanol or isopropanol or a mixyure of ethanol and isopropanol;
    b. combining the solution with water;
    c. cooling said solution to between 0 and 20° C. to form crystalline R(+)-N-propargyl-1-aminoindan; and
    d. isolating the crystalline R(+)-N-propargyl-1-aminoindan.

5. The process of claim 4, wherein the crystalline R(+)-N-propargyl-1-aminoindan is of enhanced optical purity relative to the R(+)-N-propargyl-1-aminoindan prior to crystallization.

6. The process of claim 4, wherein the solvent used in step (a) is ethanol.

7. The process of claim 4, wherein the solvent used in step (a) is isopropanol.

8. The process of claim 4, wherein the solvent used in step (a) is a mixture of ethanol and isopropanol.

9. The process of claim 4, wherein the crystalline R(+)-N-propargyl-1-aminoindan is further characterized by a melting point of 38-39° C. when determined in an open capillary or 41° C. when determined by differential scanning calorimetry.

* * * * *